(12) United States Patent
Benefield

(10) Patent No.: US 9,345,400 B1
(45) Date of Patent: May 24, 2016

(54) OCULAR DOMINANCE TESTING APPARATUS AND METHOD

(71) Applicant: Donald W. Benefield, Gulfport, MS (US)

(72) Inventor: Donald W. Benefield, Gulfport, MS (US)

( * ) Notice: Subject to any disclaimer, the term of this patent is extended or adjusted under 35 U.S.C. 154(b) by 0 days.

(21) Appl. No.: 14/686,062

(22) Filed: Apr. 14, 2015

(51) Int. Cl.
*A61B 3/10* (2006.01)
*A61B 3/032* (2006.01)

(52) U.S. Cl.
CPC ..................................... *A61B 3/032* (2013.01)

(58) Field of Classification Search
CPC ............ A61B 3/113; A61B 3/10; A61B 3/12; A61B 3/14
USPC ............................ 351/204, 200, 205, 246, 211
See application file for complete search history.

(56) References Cited

U.S. PATENT DOCUMENTS

| | | | |
|---|---|---|---|
| 1,551,114 | A | 8/1925 | Parson |
| 3,414,349 | A | 12/1968 | Vencel et al. |
| H293 | H | 6/1987 | Task et al. |
| 5,309,185 | A | 5/1994 | Harper |
| 5,349,397 | A | 9/1994 | Monahan |
| 5,413,346 | A | 5/1995 | Hedlund et al. |
| 6,644,811 | B2 | 11/2003 | Saladin |
| 7,628,489 | B2 | 12/2009 | Clark |
| 2014/0016090 | A1 * | 1/2014 | Bonnin .................. A61B 3/113 351/204 |

FOREIGN PATENT DOCUMENTS

| | | |
|---|---|---|
| CN | 101828898 A | 9/2010 |
| JP | 2006122661 A | 5/2006 |
| JP | 2009207569 A | 9/2009 |

OTHER PUBLICATIONS www.basc.org.uk/en/how-to/shooting/eye-dominance-test.cfm for an Internet site featuring an eye dominance test.
www.usaeyes.org/lasik/library/dominant-eye-test.pdf for an Internet site featuring a dominant eye test card.
www.topendsports.com/testing/tests/eye-dominance.htm for an Internet site featuring an eye dominance test.
learningsimplified.net/eye-dominance for an Internet site featuring an eye dominance test.

* cited by examiner

*Primary Examiner* — Hung Dang
(74) *Attorney, Agent, or Firm* — Bush Intellectual Property Law; Kenneth M. Bush

(57) ABSTRACT

An ocular dominance testing apparatus and method for determining a person's dominant eye wherein the method comprises the steps of fixing a target at a predetermined distance from the person, placing an ocular dominance testing apparatus between the person and the target wherein the apparatus comprises a viewing piece having a central opening therethrough, focusing both eyes on the target through the opening, closing and reopening the right eye to determine whether the target appears to move or change color, focusing both eyes on the target through the opening, and closing and reopening the left eye to determine whether the target appears to move or change color. The dominant eye is identified as the eye that appears to move the target or change the color around the target when closed and reopened.

16 Claims, 3 Drawing Sheets

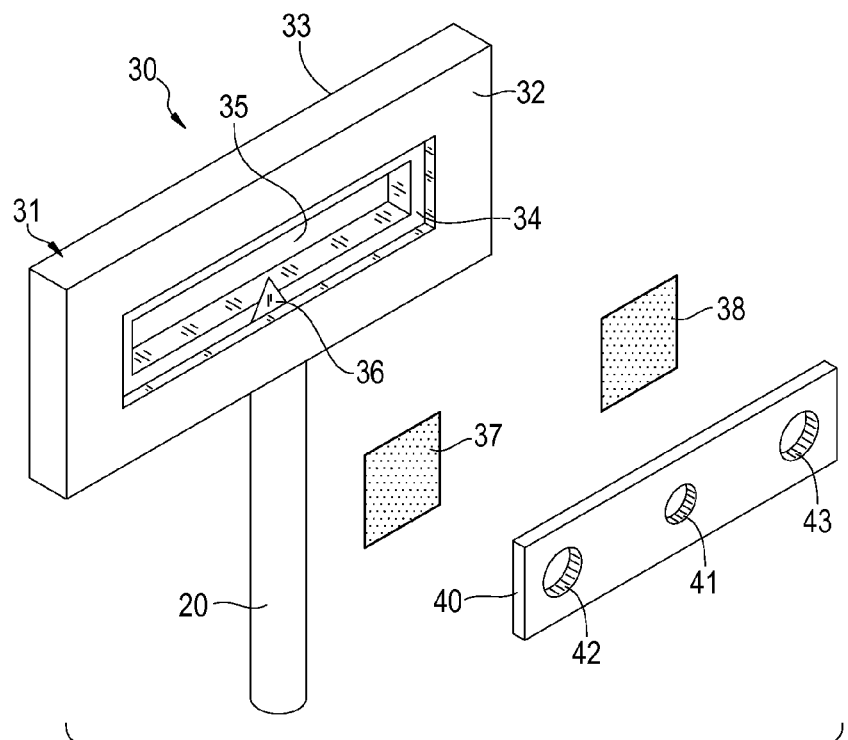
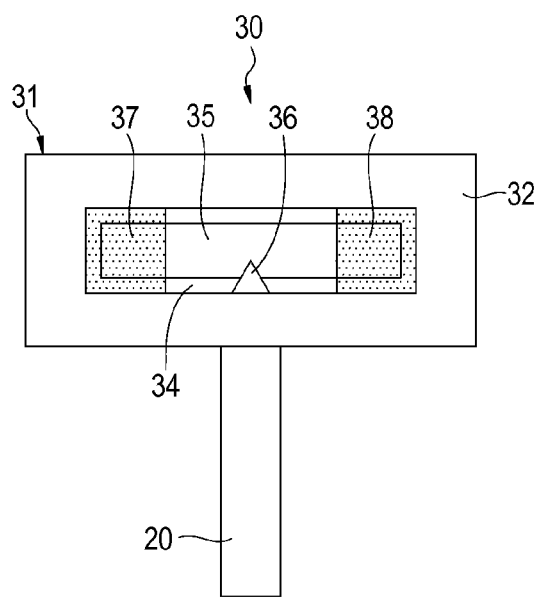
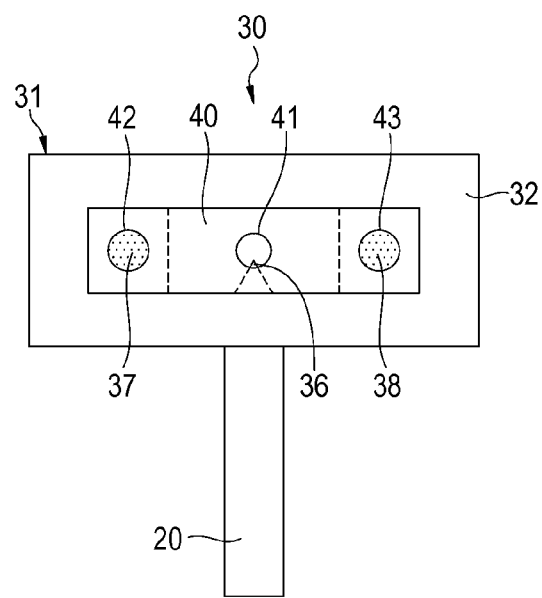
FIG. 5
FIG. 6
FIG. 7

OCULAR DOMINANCE TESTING APPARATUS AND METHOD

FIELD OF THE INVENTION

The present invention is directed to devices and methods for determining a person's dominant eye.

BACKGROUND OF THE INVENTION

People typically have one eye that is dominant. The dominant eye is the preferred eye that controls the visual system. Proper alignment of the eyes has a significant effect on the ability of a person to tolerate and to adapt to new glasses, contact lenses, monovision, lens implants, laser vision correction and other eye surgery. Eye dominance detection is extremely important in successful monovision, contact lenses, eyeglasses and eye surgery. Detecting the correct dominant eye can make a difference in obtaining a successful outcome and having a satisfied patient. It can also help explain why a patient is having difficulty with their vision.

Eye surgeons often desire to perform surgery on the non-dominant eye first to allow for a smoother neuroadaptation. With monovision situations, the non-dominant eye is usually preferred as the near vision eye. Surgical situations being more permanent, it can be of paramount importance to know the correct dominant eye in the preoperative stage. This can increase acceptance of the visual experience and even increase safety by improving visual performance and reoperations. Maximizing the ability of the dominant eye and optimizing binocular performance with the non-dominant eye may affect a person's ability to use tools, a person's coordination, aiming at a target, playing a musical instrument, driving a car, and other activities requiring synchronization of eye and hand movements involving daily life. Because of the increasingly availability of complex eyewear, surgery and implanted devices, it is desirable to have simple, rapid methods to determine the dominant eye of an individual. The knowledge of eye dominance is important and has widespread implications and significance.

What is needed is a simple handheld device and method for determining a person's dominant eye.

SUMMARY OF THE INVENTION

An ocular dominance testing apparatus and method for determining a person's dominant eye, wherein the method comprises the steps of fixing a target at a predetermined distance from the person, placing an ocular dominance testing apparatus between the person and the target wherein the apparatus comprises an opaque viewing piece having a central opening therethrough, focusing both eyes on the target through the central opening, closing and reopening the right eye to determine whether the target appears to move or change color, refocusing both eyes on the target through the opening, and closing and reopening the left eye to determine whether the target appears to move or change color. The dominant eye is identified as the eye that appears to move the target or change the color around the target when closed and reopened. The apparatus is placed in front of the person preferably from 12 to 30 inches from the eyes of the person. The target is preferably on the 20/400 line of a Snellen vision chart.

These and other features of the invention will become apparent from the following detailed description of the invention.

BRIEF DESCRIPTION OF THE DRAWINGS

FIG. 5 is an exploded rear perspective view of an alternate embodiment ocular dominance testing device of the present invention.

FIG. 6 is a rear elevation view of the ocular dominance testing device of FIG. 5 without the insert.

FIG. 7 is a rear elevation view of the ocular dominance testing device of FIG. 5 with the insert.

Figure 1:
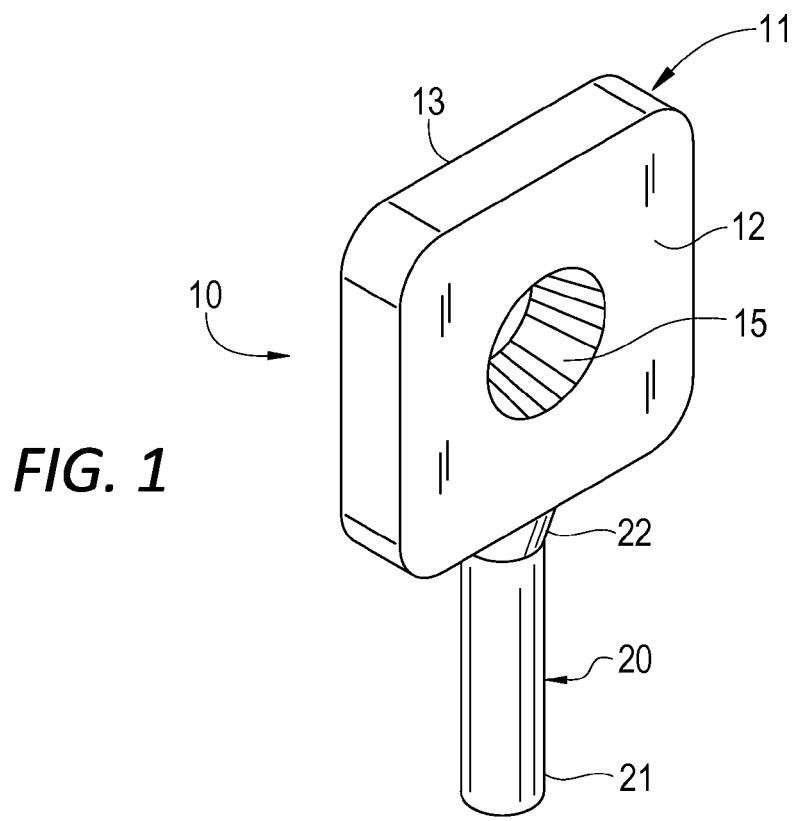
FIG. 1 is a rear perspective view of an ocular dominance testing device of the present invention.

When the terms "top," "bottom," "right," "left," "front," "rear," "first," "second," "inside," "outside," and similar terms are used, the terms should be understood in reference to the orientation of the implementations shown in the drawings and are utilized to facilitate description thereof.

DETAILED DESCRIPTION OF THE INVENTION

Figure 2:
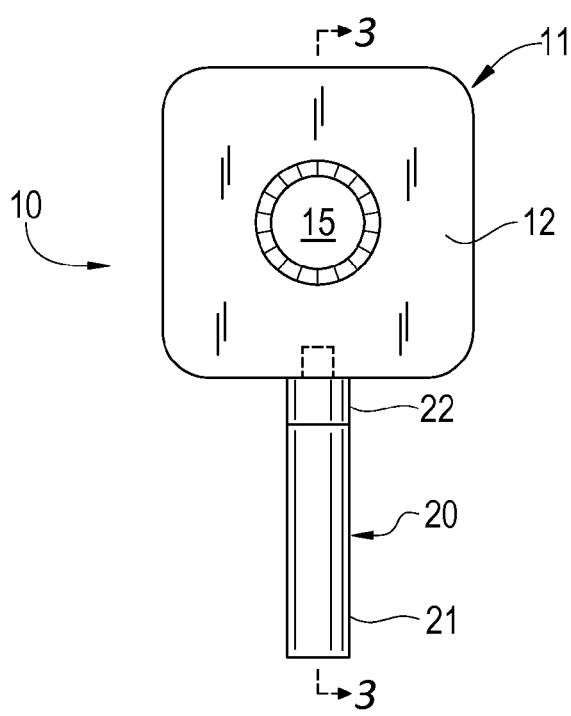
FIG. 2 is a rear elevation view of the ocular dominance testing device of FIG. 1.
Figure 3:
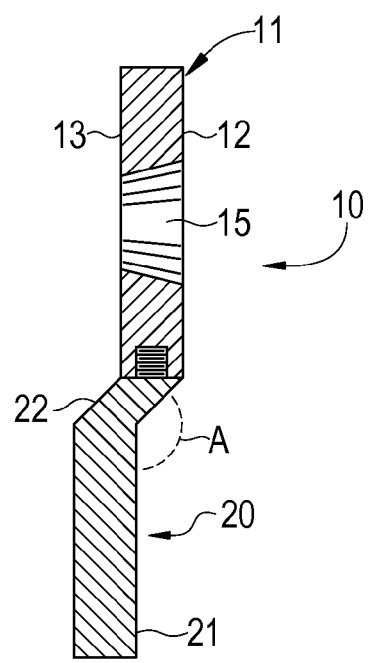
FIG. 3 is a side sectional view of the ocular dominance testing device taken along line 3-3 of FIG. 2.
Figure 4:
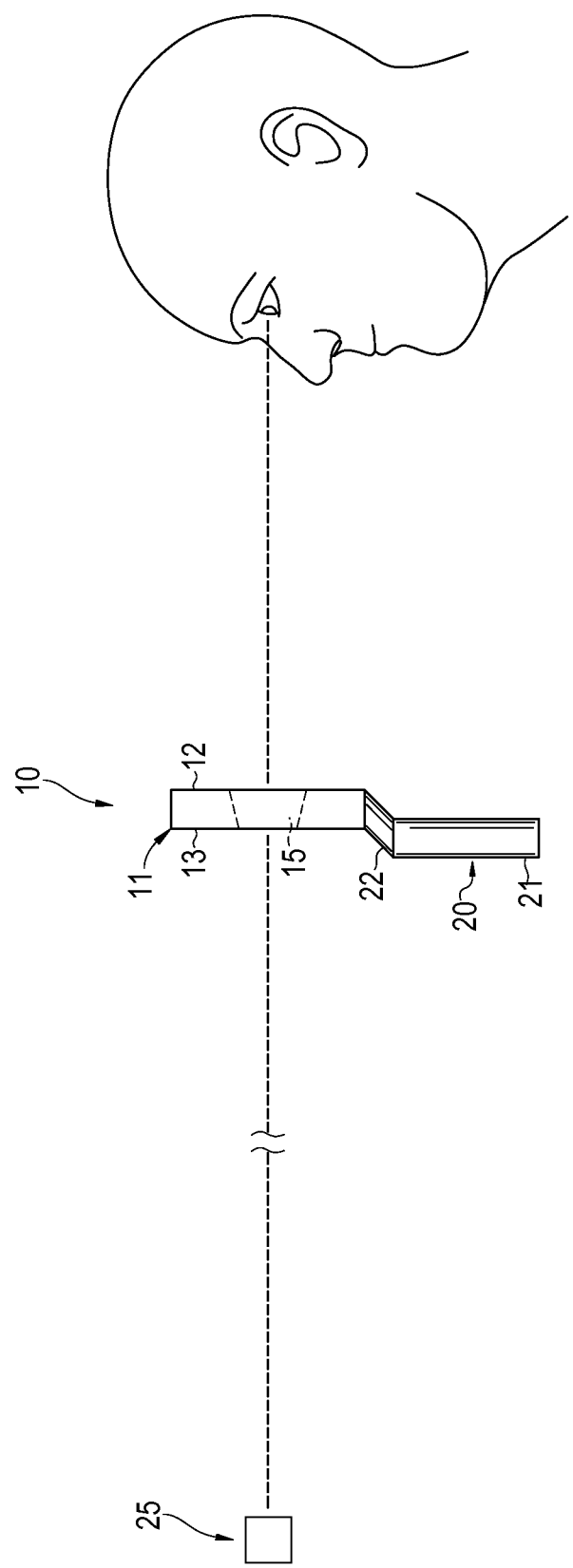
FIG. 4 is a side view of the ocular dominance testing device illustrating use by a patient.

A preferred embodiment of the present invention is shown in FIGS. 1-4, wherein the invention comprises an ocular dominance testing apparatus 10 and method of using the apparatus 10 to determine eye dominance. The apparatus 10 preferably comprises an opaque viewing piece 11 having an attached cylindrical handle 20. The viewing piece 11 is preferably a flat plate having a square shape with rounded corners. The thickness of the plate is preferably about 1 inch. The height and width of the plate are preferably at least 4 inches to block an adequate field of vision, but no greater than 24 inches so that it is still conveniently portable. The preferred height and width of the plate are about 5 inches. The viewing piece 11 has a central opening 15 therethrough, preferably from 0.5 inch to 4 inches in diameter, most preferably 1.5 to 2 inches in diameter. The opening 15 may be conical, being wider at the rear face 12 of the viewing piece 11 relative to the front face 13 of the viewing piece 11. For example, the opening 15 may be 2 inches in diameter at the rear face 12 and 1.5 inches in diameter at the front face 13. The handle 20 preferably has a lower section 21 for gripping and an angled upper section 22 that is coupled to the viewing piece 11. The angle A between the lower section 21 and the upper section 22 is preferably 45 degrees for ergonomic comfort.

In use, both eyes are preferably tested to determine eye dominance. The apparatus 10 is held by the patient by the handle 20 with the patient's arm extended such that the apparatus is from 12 to 30 inches from the eyes. The apparatus 10 is oriented such that the front face 13 of the viewing piece 11 faces a suitable target 25, such as an item (e.g. letter) on a vision chart (e.g. Snellen chart). The target 25 is distant and at least one millimeter in diameter. The 20/400 line on an eye chart is preferable and readily available in eye clinics. The chart is adjusted for 20 feet distance directly in front of the patient. The patient views the target 25 on the eye chart with both eyes open and looking through the opening 15. To test the right eye, the right eye is closed and reopened. If the target 25 appears to move then the right eye is presumed dominant. With both eyes open again, the left eye is then closed and reopened. If the target 25 does not appear to move, this confirms the right eye is dominant. To test the left eye, the patient views the target 25 on the eye chart with both eyes open and looking through the opening 15. The right eye is then closed and reopened. If the target 25 does not appear to move then the left eye is presumed dominant. With both eyes open again, the left eye is closed and reopened. If the target 25 appears to move, this confirms the left eye is dominant.

Alternate embodiments of the present invention are shown in FIGS. 5-8, wherein the ocular dominance testing apparatus 30 preferably comprises a viewing piece 31 having a rectangular shape. The height of the viewing piece 31 is preferably about 4 inches and the width of the viewing piece 31 is preferably about 9 inches. The viewing piece 31 has a central opening 35 therethrough, wherein the opening 35 is preferably rectangular in shape with a preferred height of about 1.5 inches and a preferred width of about 6.25 inches. The rear face 32 of the viewing piece 31 preferably has a recessed shoulder 34 forming a perimeter around the central opening 35. A central target marker 36 preferably extends into the bottom of the central opening 35 to assist the user with proper alignment of the apparatus 30 with the target 25. A transparent colored left pane 37 is preferably affixed across the left side of the central opening 35 and a transparent colored right pane 38 is preferably affixed across the right side of the central opening 35. The height and width of the panes 37, 38 are preferably 1.5 inches. An optional insert 40 can be removably inserted into the central opening 35 wherein the insert 40 abuts the recessed shoulder 34. The insert 40 includes a central hole 41, preferably having a diameter of 0.6875 inch, which aligns with the target marker 36, best shown in FIG. 7. The insert 40 further includes a left hole 42, preferably having a diameter of 0.875 inch, which aligns with the left pane 37, and a right hole 43, preferably having a diameter of 0.875 inch, which aligns with the right pane 38. The left hole 42 and right hole 43 are preferably spaced from the central hole 41 about 1.625 inches. The holes 41, 42, 43 are preferably circular in shape, but other shapes (e.g. elliptical, square) can be used. The left pane 37 and the right pane 38 are preferably different colors, for example, the left pane 37 can be red and the right pane 38 can be green. Alternatively, the insert 40 can be permanently affixed within the central opening 35 so that the viewing piece 31 has a central hole 41, a left hole 42, and a right hole 43, wherein the left hole 42 has a colored pane 37 and the right hole 43 has a colored pane 38.

In use, both eyes are preferably tested to determine eye dominance. The apparatus 30 is held by the patient by the handle 20 with the patient's arm extended such that the apparatus is from 12 to 30 inches from the eyes. The apparatus 30 is oriented such that the front face 33 of the viewing piece 31 faces a suitable target 25, described above. The patient views the target 25 on the eye chart with both eyes open and looking through the central opening 35 above marker 36 (and through central hole 41 if present). To test the right eye, the right eye is closed and reopened. If the target 25 appears to move and the target area changes color (e.g. turns red) then the right eye is presumed dominant. This occurs because the non-dominant left eye is aligned with the target 25 through the left pane 37 (and through the left hole 42 if present). With both eyes open again, the left eye is then closed and reopened. If the target 25 does not appear to move and the target area does not change color, this confirms the right eye is dominant. To test the left eye, the patient views the target 25 on the eye chart with both eyes open and looking through the central opening 35 above marker 36 (and through central hole 41 if present). The right eye is then closed and reopened. If the target 25 does not appear to move and the target area does not change color, the left eye is presumed dominant. With both eyes open again, the left eye is closed and reopened. If the target 25 appears to move and the target area changes color (e.g. turns green), this confirms the left eye is dominant. This occurs because the non-dominant right eye is aligned with the target 25 through the right pane 38 (and through the right hole 43 if present).

An advantage of the ocular dominance testing apparatus is that it is portable and small enough to be available in every exam room or easily moved between rooms. The method of the present invention tests ocular dominance by having the patient hold a handheld device extended away from the face toward a distant target, focus both eyes on the target through a central opening in the device, and then close an eye and reopen it to determine whether the target moves or changes color. The colored panes provide a more noticeable change to the target during testing, thus facilitating medical personnel in correctly identifying the dominant eye. Differently colored panes further facilitates medical personnel in correctly identifying the dominant eye. With expanding new vision technology in eyeglasses, contact lenses, laser vision, lens implant surgery and other emerging refractive eye surgeries, it is desirable to have a simple, easy, portable, comfortable and rapid method for determining ocular dominance.

While the invention has been shown and described in some detail with reference to specific exemplary embodiments, there is no intention that the invention be limited to such detail. On the contrary, the invention is intended to include any alternative or equivalent embodiments that fall within the spirit and scope of the invention as described above and as recited in the appended claims.

The invention claimed is:

1. A method for determining a person's dominant eye, comprising the steps of:
   1) fixing a target at a predetermined distance from the person;
   2) placing an ocular dominance testing apparatus between the person and said target, wherein said apparatus comprises an opaque viewing piece supported by a subjacent handle, said viewing piece having a central opening therethrough;
   3) focusing both eyes on said target through said opening;
   4) closing and reopening the right eye to determine whether said target appears to move;
   5) focusing both eyes on said target through said opening; and
   6) closing and reopening the left eye to determine whether said target appears to move;
   7) wherein the dominant eye is identified as the eye that appears to move said target when closed and reopened.

2. The method according to claim 1, wherein said viewing piece has a height of 5 inches, a width of 5 inches, and a thickness of 1 inch.

3. The method according to claim 1, wherein said central opening through said viewing piece is a circular opening from 1.5 to 2 inches in diameter.

4. The method according to claim 1, wherein said central opening through said viewing piece is a conical opening.

5. The method according to claim 1, wherein said central opening is rectangular in shape and said testing apparatus further comprises a central target marker, a transparent colored left pane affixed across a left side of said central opening, and a transparent colored right pane affixed across a right side of said central opening.

6. The method according to claim 5, wherein said viewing piece has a height of 4 inches, a width of 9 inches, and a thickness of 1 inch.

7. The method according to claim 6, wherein said central opening has a height of 1.5 inches and a width of 6.25 inches.

8. The method according to claim 5, wherein said testing apparatus further comprises a removable insert for insertion within said central opening, said insert having a central hole that aligns with said target marker, a left hole that aligns with said left pane, and a right hole that aligns with said right pane.

9. The method according to claim 8, wherein said insert has a height of 1.5 inches and a width of 6.25 inches.

10. The method according to claim 8, wherein said central hole has a diameter of 0.6875 inch, said left hole has a diameter of 0.875 inch, and said right hole has a diameter of 0.875 inch.

11. The method according to claim 1, wherein said apparatus is placed from 12 to 30 inches from the eyes of the person.

12. The method according to claim 1, wherein said target is on the 20/400 line of a vision chart.

13. A method for determining a person's dominant eye, comprising the steps of:
   1) fixing a target at a predetermined distance from the person, wherein said target is on the 20/400 line of a vision chart;
   2) placing an ocular dominance testing apparatus between the person and said target, wherein said apparatus is placed from 12 to 30 inches from the eyes of the person, wherein said apparatus comprises a viewing piece supported by a subjacent handle, said viewing piece having a central conical opening therethrough;
   3) focusing both eyes on said target through said opening;
   4) closing and reopening the right eye to determine whether said target appears to move;
   5) focusing both eyes on said target through said opening; and
   6) closing and reopening the left eye to determine whether said target appears to move;
   7) wherein the dominant eye is identified as the eye that appears to move said target when closed and reopened.

14. A method for determining a person's dominant eye, comprising the steps of:
   1) fixing a target at a predetermined distance from the person, wherein said target is on the 20/400 line of a vision chart;
   2) placing an ocular dominance testing apparatus between the person and said target, wherein said apparatus is placed from 12 to 30 inches from the eyes of the person, wherein said apparatus comprises a viewing piece supported by a subjacent handle, said viewing piece having a central rectangular opening therethrough, a central target marker, a transparent colored left pane affixed across a left side of said central opening, and a transparent colored right pane affixed across a right side of said central opening;
   3) focusing both eyes on said target through said opening;
   4) closing and reopening the right eye to determine whether said target appears to move or change color;
   5) focusing both eyes on said target through said opening; and
   6) closing and reopening the left eye to determine whether said target appears to move or change color;
   7) wherein the dominant eye is identified as the eye that appears to move said target or change the color around said target when the eye is closed and reopened.

15. The method according to claim 14, wherein said testing apparatus further comprises a removable insert for insertion within said central opening, said insert having a central hole that aligns with said target marker, a left hole that aligns with said left pane, and a right hole that aligns with said right pane.

16. A method for determining a person's dominant eye, comprising the steps of:
   1) fixing a target at a predetermined distance from the person, wherein said target is on the 20/400 line of a vision chart;
   2) placing an ocular dominance testing apparatus between the person and said target, wherein said apparatus is placed from 12 to 30 inches from the eyes of the person, wherein said apparatus comprises a viewing piece supported by a subjacent handle, said viewing piece having a central hole, a left hole, a right hole, a central target marker aligned with said central hole, a transparent colored left pane affixed within said left hole, and a transparent colored right pane affixed within said right hole;
   3) focusing both eyes on said target through said central hole;
   4) closing and reopening the right eye to determine whether said target appears to move or change color;
   5) focusing both eyes on said target through said central hole; and
   6) closing and reopening the left eye to determine whether said target appears to move or change color;
   7) wherein the dominant eye is identified as the eye that appears to move said target or change the color around said target when the eye is closed and reopened.

* * * * *